United States Patent [19]

Richter et al.

[11] Patent Number: 4,477,314
[45] Date of Patent: Oct. 16, 1984

[54] METHOD FOR DETERMINING SUGAR CONCENTRATION

[75] Inventors: Gerhard Richter, Erlangen; Günter Luft, Lauf; Ulrich Gebhardt, Langensendelbach, all of Fed. Rep. of Germany

[73] Assignee: Siemens Aktiengesellschaft, Berlin and Munich, Fed. Rep. of Germany

[21] Appl. No.: 515,704

[22] Filed: Jul. 20, 1983

[30] Foreign Application Priority Data

Jul. 30, 1982 [DE] Fed. Rep. of Germany ....... 3228551

[51] Int. Cl.$^3$ ............................................. G01N 27/52
[52] U.S. Cl. .................................. 204/1 T; 128/635; 204/402
[58] Field of Search ............... 204/1 T, 1 P, 1 E, 403, 204/402, 406, 415; 128/635

[56] References Cited

U.S. PATENT DOCUMENTS

| 3,920,969 | 11/1975 | Berglas | 204/1 E X |
| 4,105,522 | 8/1978 | Friedenberg et al. | 204/403 X |
| 4,127,448 | 11/1978 | Schick et al. | 204/1 T |
| 4,340,458 | 7/1982 | Lerner et al. | 128/635 X |
| 4,366,033 | 12/1982 | Richter et al. | 204/1 T |

FOREIGN PATENT DOCUMENTS 1422172 1/1976 United Kingdom .

OTHER PUBLICATIONS

"Transactions of American Society Artif. Int. Organs," vol. XIX, 1973, pp. 352-360.
"Biomed Technik", 22 (1977), Supplement Volume, pp. 399-400.

Primary Examiner—G. L. Kaplan
Assistant Examiner—Nam X. Nguyen
Attorney, Agent, or Firm—Karl F. Milde, Jr.

[57] ABSTRACT

A method for determining the concentration of sugar in the presence of interfering foreign substances, by means of a test electrode with a membrane placed in front of it, the electrode being contained in an electrocatalytic sugar sensor, whereby the test electrode is set potentiostatically to a reactivation potential and to a test potential and the current flowing during the set test period is evaluated as a test signal. The invention formulates a method such that with varying concentrations of urea a sensitive determination of sugar concentration which is reliable over a long term is achieved. The invention discloses the method which includes the step that after the reactivation potential and prior to the test potential a third potential that is more negative than the test potential is applied to the test electrode. The technique proposed in the invention is particularly appropriate for the determination of the concentration of glucose in body fluids.

9 Claims, No Drawings

METHOD FOR DETERMINING SUGAR CONCENTRATION

BACKGROUND OF THE INVENTION

The invention relates to a method for determining the concentration of sugar in the presence of foreign substances, in particular for the determination of glucose in a body fluid. This is accomplished by means of a device which includes a test electrode with a membrane placed in front of it the electrode being contained in an electrocatalytic sugar sensor, whereby the test electrode is set to a reactivation potential and to a test potential and whereby the current flowing during the test period—after a time delay with reference to the beginning of the test period—is evaluated as a test signal.

The determination of the concentration of sugar in a body fluid, particularly in a patient's blood, is significant, for example, to diagnose or evaluate diabetics. For a diabetic patient, whose natural regulation of body glucose is disturbed, it is thus important that the normal blood glucose level as artificially maintained to be as constant as possible over the course of the day. The blood glucose level can be influenced by diet, insulin injections and by physical therapy. It is essential in this regard that an overcompensation or an undercompensation of the sugar content in the blood be avoided. A patient himself, must be aware of the blood sugar content to be able to use appropriate measures as necessary for control of his or her sugar levels.

The automatic regulation of the glucose concentration by means of an artificial Beta cell has been considered, whereby the insulin supply to the blood is controlled by a glucose sensor such that whenever a deviation occurs from an ideal glucose level insulin is introduced into the blood in proportion to the deviation from the ideal level.

Until now glucose determination in the blood has been measured, in general, externally in the laboratory by photometric methods. There are, however, also electrochemical sensors that provide a direct determination of the glucose in the body fluid. In these so-called enzyme sensors, the glucose is oxidized with the aid of glucose oxidase into gluconic acid, such that oxygen is consumed and hydrogen peroxide is formed. The consumption of oxygen as well as the hydrogen peroxide formation can be electrochemically measured and thus a signal can be obtained that is related to the concentration of glucose. Since enzyme sensors operate selectively and do not react to foreign substances, a reproducible determination of glucose is possible. However, such sensors do not lend themselves to long-term implantation, because the enzymes, as any other proteins, decay over time under physiological conditions, i.e. they do not have long-term stability when introduced into a human body.

An electrocatalytic glucose sensor has been made known through British Pat. No. 1,422,172. This sensor, when operated in a voltage control mode, is however not stable over long term; whereas, on the other hand, when operated in a current control mode the sensitivity does not achieve a desired accuracy.

With electrocatalytic glucose sensors intermittent measurements over time are possible, especially relative measurements (cf. "Trans. Amer. Soc. Artif. Int. Organs", Vol. XIX, 1973, pp 352-360). However, disturbances of the test signal by coreactants always occur. Impurities can be oxidized at the test electrode thereby providing an inaccurate test signal or can reduce the activity of the test electrode by blocking. With implantable sensors, components of body fluids, especially urea and amino acids, have exhibited interference, preventing the generation of reproducible, long-term measurements.

The above shortcomings also apply to an implantable electrocatalytic glucose sensor such as the one described in the journal "Biomed Technik", 22 (1977), Supplement Volume, pp 399-400. This sensor, which has a test electrode, a counter electrode, and a reference electrode, is driven by the so called potential step method, i.e. the test electrode has alternately applied to it a test potential and a reactivation potential which is more positive with reference to the test potential. During the test period the current is integrated and the integral thus obtained represents the test signal at the end of the test period.

A sensitive and reliable glucose determination, even in body fluids, involves the method published in U.S. Pat. No. 4,366,033 in which the evaluation of the current after a time delay with respect to the beginning of the test period is undertaken and in which a membrane, placed in front of the test electrode of the electrocatalytic sugar sensor, impedes the supply of interfering foreign substances to the test electrode in such a way that a diffusion limiting current is set up in the reactivation phase upon oxidation of the foreign substances. A reliable determination of the glucose concentration over a longer period of time turns out to be difficult if varying concentrations of urea are present in the body fluid. Then the glucose test signal can be relatively strongly influenced such that significant errors occur in the glucose determination. However, in a continuous blood sugar determination varying concentrations of urea must always be taken into consideration.

SUMMARY OF THE INVENTION

The object of the invention is to disclose a method for the determination of sugar concentrations, avoiding the problems discussed above, in which a reactivation potential and a test potential are applied to a test electrode, and to render the method in such a way that a sensitive, reliable, long-term determination of sugar is achieved even in the presence of varying concentrations of urea.

This is achieved by this invention by means of the fact that a third potential is applied to the test electrode for a short period of time after the reactivation potential and prior to the test potential and this third potential is more negative than the test potential.

The third potential, hereinafter referred to as the reduction potential, is thus more negative than the test potential. Since the test potential itself is more negative than the reactivation potential, the test potential magnitude ranges between the reduction potential and the reactivation potential.

These potentials attain special significance in accordance with the method of this invention, as described below in greater detail.

DETAILED DESCRIPTION

Since the interfering foreign substances accompanying glucose are in general more heavily oxidizable than glucose, the glucose determination should be possible principally under mild oxidation conditions. In practice, however, this is not the case, since other accompanying adhesive substances block the electrode or catalyst surfaces. The removal of this block is accomplished, however, if the test electrode is oxidized with a strongly anodic potential and if simultaneously an impermeable membrane in front of the electrode impedes the supply of the substances effecting the block. This applies primarily to blockages caused by amino acids.

Due to the small size of the urea molecule with respect to glucose and due to its similar concentration levels in the blood along with glucose, urea also diffuses through the membrane placed in front of the test electrode. This urea presumably limits the reduction of the oxide layer formed on the electrode surface during the reactivation potential, for example on a platinum electrode, and thus delays the glucose oxidation effected during the test potential. With the method proposed by this invention an improved glucose signal during the test potential is achieved by means of the fact that a negative potential, negative with respect to the test potential, is applied to the electrode briefly prior to the test itself. Thus the limitation of the reduction of the (platinum) oxide layer by urea is increased or the reduction of the oxide is accelerated. In this manner during the test potential an improved sensitivity is achieved for the determination of glucose.

The duration of the reduction potential applied to the test electrode is preferably from 1 to 10 seconds. The reactivation and the test are performed in general over a longer period. So the reactivation potential can, for example, be applied for 50 seconds to the test electrode and the test potential for 40 seconds. A test potential duration of 20 seconds is sufficient, for example.

For the three different potential levels according to the proposed invention the following represent preferred values:

the reactivation potential is greater than 800 mV and lies preferably between 1200 and 1600 mV;
the test potential lies between 200 and 800 mV and is preferably approximately 400 mV;
the reduction potential is less than 200 mV and is preferably approximately 100 mV.

The potential values are referenced to the potential of the reversible hydrogen electrode in the same electrolyte.

The setting of the reduction potential is accomplished in accordance with the present invention preferably such that the reactivation potential, the reduction potential and the test potential are sequentially potentiostatically applied to the test electrode. The setting of the reduction potential can, however, be accomplished in another manner:

1. After reactivation the desired negative potential is achieved potentiostatically; the reduction potential can be up to 0.4 volts more negative than the test potential. The negative potential can also be controlled potentiodynamically, especially with a triangular progression, and in the same manner the shift to the test potential can be effected subsequently.

2. In connection with the reactivation phase a cathode current is controlled to flow in such a manner that a given charge is converted which suffices to achieve the reduction potential. Thus the double layer capacitance is discharged and the reduction of the (platinum) oxide and of the absorbed reaction products is accelerated.

3. If the ohmic voltage drop between the test electrode and the reference electrode is compensated, which can be done with a potentiostat, then the desired goal can be achieved by a specific overcompensation. At the switch from the reactivation potential to the test potential, an overshoot is produced by means of which a potential is temporarily set that is more negative than the test potential, i.e., the reduction potential. In practice a voltage drop is generated in the test circuit between the test electrode and the potentiostat by switching in a small ohmic resistance and this drop is adapted to the voltage drop that occurs between the test electrode and the reference electrode by negative amplification with an amplification factor equal to or greater than 1. This voltage is added to the reference voltage at the input of the potentiostat. An overshoot is achieved whenever the amplification is selected to be slightly greater than required.

The goal of the methods mentioned above is thus a rapid reduction of the oxide layer on the test electrode, so that the electrode will possess an optimal activity to measure glucose for the duration of the test potential. An increase of the activity of the electrode itself above a certain level is not useful, because a higher level of reduction activity causes a greater thickness of the active layer and thus in turn causes a time delay which strongly affects the energy consumption of the system. A raising of the electrode potential is further not even possible, because over a certain potential the development of oxygen begins and the sugar sensor used becomes unusable as soon as gas collects between the electrode and the membrane. In the methods proposed in the invention the reactivation, as already mentioned, is achieved advantageously at a potential $\psi_7 > 800$ mV; preferably the reactivation potential lies between 1200 mV and 1600 mV. The permissible value depends on the duration of the reactivation. Thus no gas generation occurs within a time span of approximately 25 seconds even at 1600 mV.

An electrocatalytic sugar sensor for the performance of the technique proposed in the invention possesses a test electrode, a counterelectrode and a reference electrode with a hydrophilic membrane arranged in front of the active surface of the test electrode. The potential of the test electrode is, for example, controlled by a potentiostat, aided by a timer, so that the three potentials are sequentially adjusted. The current flowing during the test potential is then evaluated, preferably by an integrator.

Permeability and thickness of the membrane placed in front of the electrode are not optionally selectable. They are more determined by the desired diffusion limit of the test signal and by the desired duration of the test. The time constant of the sugar sensor is dependent on these values: it is determined by $\tau = 0.167 \, d^2/D$; where d is the thickness of the membrane and D is the diffusion coefficient. To set the diffusion limit reliably, as small a diffusion coefficient as possible is attempted, namely a diffusion coefficient of $D < 10^{-8}$ cm$^2$/sec, whereby the lower limitation is given by the technical considerations for current measurement. To simultaneously achieve the required time constant, of less than 10 minutes, the membrane should preferably possess a thickness of $d < 50$ μm.

Manufacturing of membranes with as low a permeability as indicated above can advantageously be started with relatively hydrophobic film-forming plastics such as polyethylene, polytetrafluoroethylene and silicone caoutchouc, which can be made hydrophilic by appropriate measures in particular radiation-grafting with acrylic acid, methacrylic acid, chlorosulfonic acid or benzylamine, i.e. by radiochemical graft polymerization. Another example is a membrane made from sulfurized polysulfone.

The invention will be explained still more precisely with the aid of several examples.

EXAMPLE 1

A platinized platinum electrode with an active surface of 0.03 square centimeters is polarized according to the following program of potentials:

Reactivation potential $\psi_1 = 1500$ mV/$H_{2rev}$ (Duration: 50 seconds);

Reduction potential $\psi_2 = 100$ mV/$H_{2rev}$ (Duration: 10 seconds);

Test potential $\psi_3 = 400$ mV/$H_{2rev}$ (Duration: 40 seconds).

The integration of the current at the test potential is accomplished in the range of from 20 seconds to 40 seconds.

A silver/silver chloride electrode serves as the reference electrode, the counterelectrode consists of platinized platinum. A 20 micrometer thick polysulfone membrane covers the test electrode, i.e. is situated between the test electrode and the counterelectrode. The platinizing of the electrode is accomplished in a 2.5 percent solution of hexachloroplatinic acid with a current density of 30 mA.cm$^{-2}$ for a duration of 5 minutes. During the experiments a type of Tyrode's solution is used as the electrolyte that consists of 125 mmol of sodium chloride, 2.68 mmol potassium chloride, 1.8 mmol calcium chloride, 1.05 mmol magnesium chloride, 0.417 mmol sodium dihydrogen phosphate and 12 mmol of sodium hydrogen carbonate in one liter of water. To hold the oxygen partial pressure and the pH value of the solution constant it is flushed with a mixture of 95 percent air and 5 percent carbon dioxide.

At the beginning of the experiment 0.01 percent urea is added to the electrolyte. If one now follows the course of the test signal depending on the number of test periods with changes in the glucose or urea concentrations, then the following results occur. If the glucose concentration is increased in steps from an initial 0.05 percent of 0.3 percent, then the test signal follows accordingly, i.e. the transported charge increases proportionally to the glucose concentration. If then at the highest test value, i.e. at 0.3 percent glucose, the concentration of urea is increased to 0.038 percent, then no change is produced in the test signal. If subsequently the glucose concentration is reduced in steps to 0.05 percent and then the urea concentration is returned to the minimum value, i.e. 0.01 percent, then hardly any deviation results.

EXAMPLE 2 (comparative example)

To a platinized platinum electrode (active surface: 0.03 square centimeter) as test electrode a potential curve with only two potential steps is applied:

Reactivation potential $\psi_1 = 1600$ mV/$H_{2rev}$ (Duration: 25 seconds);

Test potential $\psi_3 = 400$ mV/$H_{2rev}$ (Duration: 25 seconds).

The integration of the current at the test potential is performed during a 20 second to 25 second timeframe.

Here upon change in the concentration of glucose a test signal is also produced, however, with the addition of 0.016 percent urea (at a glucose concentration of 0.2 percent) a significant decrease in the test signal results; an additional decrease results if the urea concentration is increased to 0.038 percent. If now the glucose concentration is decreased from 0.2 percent to 0.1 percent, only a very small change in the test signal results and the same results if the glucose concentration is increased back from 0.1 percent to 0.2 percent. The electrode is thus blocked by the urea. The test signal only increases again if the concentration of urea is decreased.

EXAMPLE 3

A platinized platinum electrode as in Example 1 with an active surface of 0.125 square centimeter is polarized according to the following potentials:

Reactivation potential $\psi_1 = 1500$ mV/$H_2$ rev (Duration: 50 seconds);

Reduction potential $\psi_2 = 100$ mV/$H_2$ rev (Duration: 10 seconds);

Test potential $\psi_3 = 400$ mV/$H_2$ rev (Duration: 20 seconds).

The integration of the current at the test potential is performed during a 1 to 20 seconds range. A silver/silver chloride electrode serves as the reference electrode, the counter electrode is a platinum foil. In front of the test electrode is a membrane of polytetrafluoroethylene, which is grafted with quaternized benzylamine. The Tyrode's solution described in Example 1 served as the electrolyte.

In these examples according to this invention the simultaneous influence of urea and amino acids on the glucose test signal was investigated. The urea as well as the amino acid concentrations (a mixture of 16 amino acids normally found in adult plasma was investigated) were varied between a low physiological value and a high physiological value. It was shown that for blood glucose determination in the worst case, i.e. either with a simultaneous high or a simultaneous low amino acid and urea content, a test error of 20 percent can occur and, indeed, at a value of the physiological concentration of glucose (approximately 0.08 percent). What is essential, however, is that the technique disclosed in the invention decreases the influence of the urea and the concentration of glucose can be determined even in the presence of varying concentrations of urea and amino acids.

There has thus been shown and described novel methods for determining sugar levels in a fluid which fulfill all the objects and advantages sought therefor. Many changes, modifications, variations and other uses and applications of the subject invention will, however, become apparent to those skilled in the art after considering this specification which disclose preferred embodiments thereof. All such changes, modifications, variations and other uses and applications which do not depart from the spirit and scope of the invention are deemed to be covered by the invention which is limited only by the claims which follow.

What is claimed is:

1. An improved method for measuring the sugar content of a fluid in the presence of interfering foreign substances by means of an electrocatalytic sugar sensor which includes a test electrode having a membrane arranged in front of it, said method including the steps of applying potentiostatically to said electrode a reactivation potential and a test potential and measuring and evaluating a current flowing during a test period with a set time delay to determine sugar content said improvement including the step of:

applying a reduction potential for a period of time shorter than said test period to said test electrode to reduce the effect of said interfering foreign substances, said reduction potential being more negative than said test potential and being applied after the application of said reactivation potential and prior to the application of said test potential.

2. The method according to claim 1, wherein said reduction potential is applied to said test electrode for a time duration ranging from 1 second to 10 seconds.

3. The method as in claim 1 or 2, wherein said reactivation is greater than 800 mV, wherein said test potential lies in the range of between 200 mV and 800 mV, and wherein said reduction potential is less than 200 mV, said reactivation potential, test potential, and reduction potential being measured with reference to the potential of a reversible hydrogen electrode.

4. The method as in claim 3, wherein said reactivation potential lies in the range of between 1200 mV and 1600 mV, wherein said test potential is approximately 400 mV, and wherein said reduction potential is approximately 100 mV.

5. The method as in claim 1, wherein said reactivation potential, reduction potential and test potential are sequentially potentiostatically applied to said test electrode.

6. The method as in claim 1, wherein said reduction potential is controlled potentiodynamically and substantially linearly with time and wherein the transition from said reduction potential to said test potential is performed in the same manner.

7. The method as in claim 1, wherein the test electrode is precharged to a predetermined load after the reactivation, thereby setting the reduction potential.

8. The method according to claim 7, wherein said precharging of said test electrode to a predetermined load after the reactivation is performed galvanostatically.

9. The method as per claim 1, wherein an ohmic voltage drop between said test electrode and a reference electrode is compensated so that a certain overcompensation is set up.

* * * * *